United States Patent [19]

Ohya et al.

[11] 3,983,002

[45] Sept. 28, 1976

[54] PROCESS FOR PREPARATION OF CELLULASE

[75] Inventors: Takaichi Ohya; Nobumasa Yokoi; Tamio Mase, all of Aichi, Japan

[73] Assignee: Amano Pharmaceutical Co., Ltd., Nagoya, Japan

[22] Filed: Nov. 8, 1974

[21] Appl. No.: 522,262

[30] Foreign Application Priority Data

Nov. 10, 1973  Japan.............................. 48-125934

[52] U.S. Cl.............................. 195/66 R; 195/33; 195/62
[51] Int. Cl.$^2$...................... C12D 13/10; C07G 7/02
[58] Field of Search................ 195/66 R, 33, 65, 62, 195/96

[56] References Cited

UNITED STATES PATENTS 3,844,890  10/1974  Horikoshi et al..................... 195/62

OTHER PUBLICATIONS

Banikova et al., *Farmatsiya* (Sofia) 1971, 21(4) pp. 14–20.

Banikova, "Conditions for the Isolation of Enzymes of Aspergillus Niger Strains Used for Obtaining Citric Acid", Chemical Abstracts vol. 76, p. 316 84510W (1972).

Merkel, *J. Bacteriology*, 87(5) pp. 1227–1233 (1964).

*Primary Examiner*—A. Louis Monacell
*Assistant Examiner*—Thomas G. Wiseman
*Attorney, Agent, or Firm*—Browdy and Neimark

[57] ABSTRACT

Aeromonas sp. No. 212 is cultured to allow it to produce a novel cellulase 212 and/or novel hemicellulase in a culture medium, and the so produced cellulase 212 and/or hemicellulase 333 is separated from the culture medium.

The so separated novel cellulase 212 and/or novel hemicellulase 333 is used as a cellulosic material-decomposing agent in purifying tanks, plants for treatment of industrial waste waters, excrement treatment plants, drainage disposal treatment plants and the like.

6 Claims, 7 Drawing Figures

PROCESS FOR PREPARATION OF CELLULASE

FIELD OF THE INVENTION

This invention relates to a process for the preparation of novel cellulase and/or hemicellualse 333.

Further, the invention relates to a cellulosic material-decomposing agent for sewage treatment which comprises as an effective ingredient the so prepared cellulase 212 and/or hemicellulase 333.

BACKGROUND OF THE INVENTION

Cellulase has heretofore been used as a cellulose-decomposing enzyme in various fields, for example, in food industries, feedstuff industries and pharmaceutical industries, and recently, its use for treatment of excrement and kitchen refuse has attracted great attention in the art.

Hemicellulase is known as an enzyme decomposing hemicellulose such as xylan which is one component of straw, glucomannan which is one component of konjak and galactan which is richly contained in sea algae. Hemicellulase acts on husks of grains to decompose them and make them edible. Further, hemicellulase is used in combination with pectinase to clarify juices of citrus fruits, and when it is added to flour, it decomposes pentosan to improve the texture of bread. Moreover, when it is incorporated into roast coffee beans, the effect of extraction of the coffee extract can be heightened. Still, in addition, hemicellulase can decompose even hemicellulosic materials contained in refuse, waste water, raw sewage or the like, which cannot be decomposed by cellulase. Accordingly, uses of hemicellulase utilizing these activities have recently been developed.

SUMMARY OF THE INVENTION

Research work has been conducted with a view to screening microorganisms producing cellulase and hemicellulase from soils, and it has been found that a strain of Aeromonas, one of the aerobic bacteria can produce strong cellulase and hemicellulase enzymes and accumulate them in the culture medium. Among bacteria belonging to the genus Aeromonas, this strain is the first instance in which both an activity of producing cellulase and hemicellulase is found. It has also been found that both the cellulase and hemicellulase produced by this strain are novel, and this novel cellulase decomposes natural celluloses quite well and this novel hemicellulase decomposes straw and food residue quite well. Further, it has been found that both the enzymes have a higher alkali resistance than is processed by known enzymes and they act quite well at a pH of 4.5 to 8.5, especially at a pH of 6.0 to 8.0 in which the pH of sewage or excrement is included. When both the enzymes are used in combination in sewage disposal plants or the like, they exhibit a surprisingly high effect of decomposing cellulosic materials.

It is, accordingly, a primary object of this invention to prepare cellulase 212.

Another object of this invention is to prepare hemicellulase 333.

Still another object of this invention is to prepare simultaneously cellulase 212 and heimcellulase 333 to provide a mixed enzyme.

A further object of this invention is to provide a cellulosic material-decomposing agent for sewage treatment or the like which contains both cellulase 212 and hemicellulase 333.

DETAILED DESCRIPTION OF THE INVENTION

Figure 1:
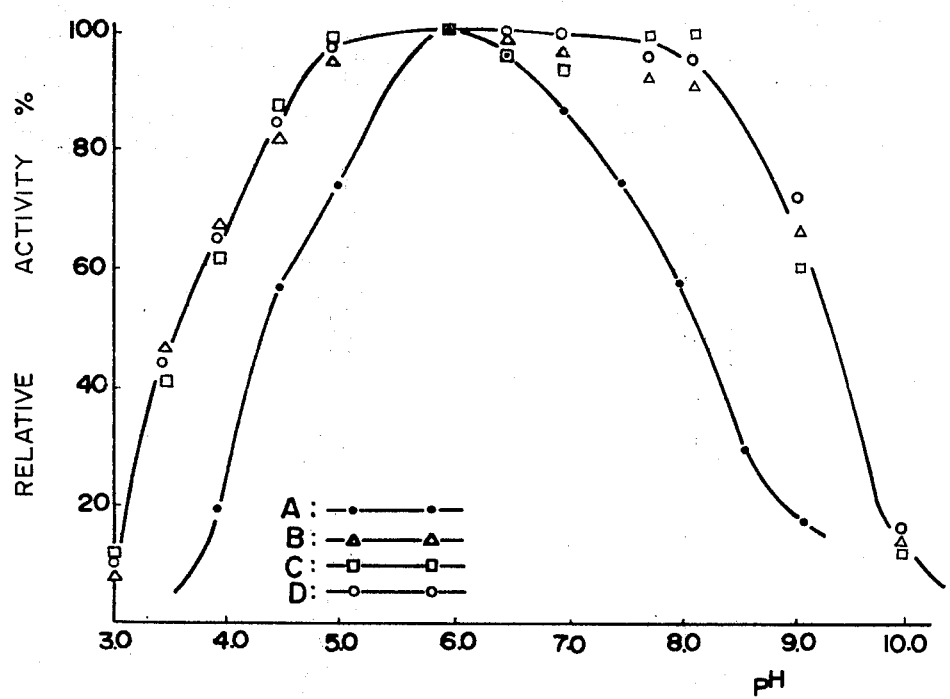
FIG. 1 shows optimum pH curves of cellulase 212, in which Curve A is for decomposition of absorbent cotton, Curve B for decomposition of filter paper, Curve C for decomposition of Avicel and Curve D for decomposition of swollen cellulose.

Aeromonas sp. No. 212 producing cellulase 212 and hemicellulase 333, which is used in this invention, has the following microbiological properties:

a. Morphology
1. Bacillus; $(0.4–0.5 \times 2.0–6.0)\ \mu$
2. Single rod or short rod
3. One polar flagellium, motility
4. No spores
5. Gram dyeing: negative
6. Acid fastness: negative B. Growth Conditions
1. Bouillon-agar plate culture: circular convex colony, smooth surface, undulate periphery, wetty gloss, viscous
2. Bouillon-agar streak culture: beaded, scanty growth
3. Bouillon liquid culture: slightly turbid, no growth on the surface, no precipitation
4. Bouillon-gelatin stub culture: not liquified
5. Litmus milk: slightly acidic, not peptonized, not coagulated C. Bio-chemical Properties:
1. Nitrate reduction: positive (in medium containing bacto-tryptone, meat extract and potassium nitrate)
2. Denitrification: positive
3. MR test: negative
4. VP test: positive
5. Formation of indole: negative
6. Formation of hydrogen sulfide: negative
7. Hydrolysis of starch: positive
8. Utilization of citric acid: negative
9. Utilization of inorganic nitrogen source: neither nitrate nor ammonium salt is utilized.
10. Formation of pigment: negative
11. Urease: negative
12. Oxidase: positive
13. Catalase: positive
14. Growth pH (cultured at 37° C. for 3 days in 1% bacto-tryptone water):

| 6.2 | 7.1 | 8.1 | 9.0 | 10.0 |

-continued

| | | | | |
|---|---|---|---|---|
| − | + | + | + | + |

15. Growth Temperature (1% bacto-tryptone water of pH of 7.5):

| 10°C. | 20°C. | 30°C. | 34°C. | 37°C. | 42°C. |
|---|---|---|---|---|---|
| − | + | + | + | ++ | + |

16. Behavior to oxygen: aerobic
17. O-F test: fermentative
18. Formation of acids and gases from saccharides (cultured in medium containing 2 g/l of peptone, 5 g/l of sodium chloride, 0.3 g/l of dipotassium phosphate, 0.03 g/l of bromocresol purple and 15 g/l of agar):
  a. Formation of acids: as shown in Table I below
  b. Formation of gases: negative

TABLE I

| Saccharide | Formation of acid |
|---|---|
| L-arabinose | + |
| Trehalose | + |
| D-xylose | + |
| D-sorbitol | + |
| D-glucose | + |
| D-mannitol | + |
| Inositol | − |
| D-fructose | + |
| Glycerine | − |
| Maltose | + |
| Starch | + |
| Sucrose | + |
| D-galactose | + |
| Lactose | + |

The foregoing microbiological properties have been determined according to the teachings of *Manual of Microbiological Method* (compiled by American Society of Bacteriology) and *Manual of Bacteriological Practice* (compiled by Institute of Research in Infectious Diseases, University of Tokyo), and when these microbiological properties are examined in light of disclosures of Bergey's *Manual of Determinative Bacteriology*, 7th Edition, in view of the fact that this strain is a bacillus having a size of 0.4 − 0.5 × 2.0 − 6.0 $\mu$ and one polar flagella with motility, it forms no spores and is Gram-negative, catalase-positive, oxidase-positive and aerobic and that it decomposes saccharides fermentatively at the O-F test, it is considered that the microorganism belongs to the genus Aeromonas. Accordingly, this strain was named Aeromonas sp. No. 212. This strain was deposited at Fermentation Research Institute, Agency of Industrial Science and Technology with the deposition number of FERM-P No. 2306 and at American Type Culture Collection with the deposition No. of ATCC 31085.

The Aeromonas sp. No. 212 produces and accumulates high units of cellulase 212 and hemicellulase 333 in a culture medium. As the carbon source to be added to the culture medium for this strain for production of these enzymes, there can be employed various glucosides such as starch and glucose. As the nitrogen source, there can be employed ammonium salts such as ammonium sulfate, ammonium nitrate and ammonium acetate and organic substances such as peptone, meat extract, cornsteep liquor and defatted soybean. Further, a very small quantity of inorganic metal salts, vitamins and growth-promoting factors such as yeast extract are preferably added to the culture medium. Still further, cellulosic materials such as carboxymethyl cellulose (CMC), microcrystalline cellulose such as that sold under the name of Avicel and filter paper and hemicellulosic materials such as wheat bran, xylan and soybean cake are generally added to the culture medium as inducers for the enzymes. In case preparation of cellulase 212 is intended, it is preferred that a cellulosic material such as CMC, Avicel and filter paper be added, and when preparation of hemicellulase is intended, good results are obtained by incorporation of a hemicellulosic material such as wheat bran, xylan and soybean cake. On culturing, the pH of the culture medium is adjust to 7 to 10, preferably 8 to 9, by addition of sodium carbonate, sodium bicarbonate or sodium hydroxide, and it is preferred that the culturing be conducted at a temperature of about 27° to about 40°C. under shaking or aerobic agitation. The amount accumulated of the intended enzyme is largest when the culturing is continued for about 1 to 4 days. The crude enzyme can be obtained by subjecting the resulting culture medium of centrifugal separation or by adding a filter aide to the medium and filtering it. It is also possible to recover the crude enzyme by coprecipitating cells with a salt such as calcium acetate and removing the coprecipitated cells. The so recovered crude enzyme liquid can be used as it is. It is possible to recover crude enzyme powder by treating the crude enzyme liquid according to a known customary method such as salting-out with ammonium sulfate, solvent precipitation and dialysis. In some cases, the so obtained crude enzyme contains both cellulase 212 and hemicellulase 333. If the enzyme is used as the active ingredient of a cellulosic material-decomposing agent, such crude enzyme mixture can be directly used as it is. However, when cellulase 212 and hemicellulase 333 are used individually for preparation of foodstuffs or medicines, it is necessary to separate and purify both the enzymes.

In separating the crude enzyme mixture liquid into cellulase 212 and hemicellulase 333, the enzyme solution is adsorbed on DEAE-Sephadex A-50 buffered in advance with 0.05M tris-hydrochloric acid buffer solution (pH = 8.8), and the adsorbed enzyme is eluted with 0.5 M aqueous solution of sodium chloride. Then, it is further adsorbed at a pH of 7.5 on DEAE-Sephadex A-50 and eluted with 0.1 M aqueous solution of sodium chloride, to thereby collect an active fraction of cellulase 212. Then, the cellulase fraction is passed through a column packed with Sephadex G-100 buffered with 0.05M tris-hydrochloric acid buffer solution of a pH of 7.0 (containing 0.1 M of sodium chloride), and this gel filtration procedure is repeated twice to obtain a standard sample of cellulase 212 exhibiting a single band corresponding to protein activity.

On the other hand, the effluent recovered at the adsorption treatment with DEAE-Sephadex A-50 is treated so that its pH is adjusted to 8.5, and it is then adsorbed on CM-Sephadex C-50 and after washing, elution is effected with use of 0.1 M aqueous solution of sodium chloride. Then, the eluted active fraction if adsorbed on a hydroxylapatite column with use of 0.01 phosphate buffer solution of a pH of 6.8 and elution is effected with 0.05 M phosphate buffer solution of a pH of 6.8 to collect an active fraction. The fraction is subjected to gel filtration with Biogel P-60 to obtain a purified hemicellulase 333 liquid.

Cellulase 212 has the following properties.

1. Activity: It acts on cellulosic materials such as microcrystalline cellulose (Avicel), filter paper, absorbent cotton, CMC and the like and solubilizes them.

2. Substrate specificity. It acts well on filter paper, absorbent cotton, Avicel, swollen cellulose, CMC, etc.

Figure 2:
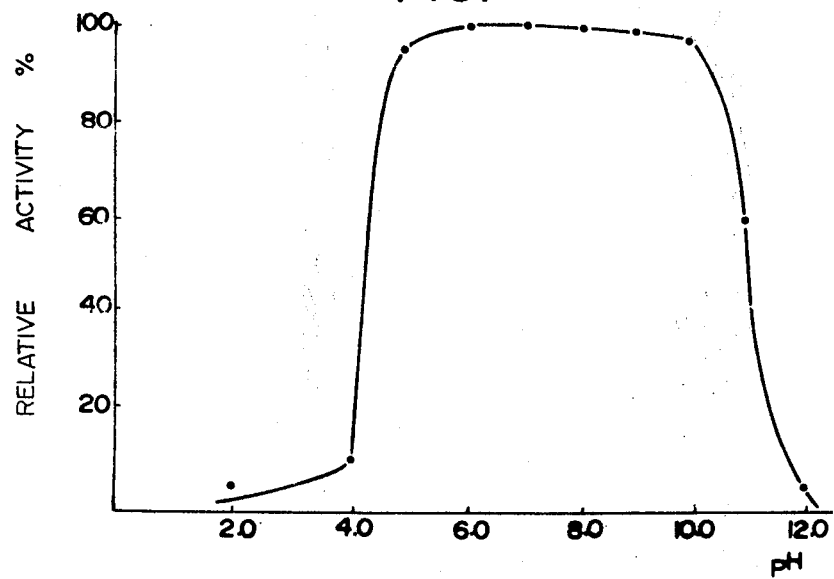
FIG. 2 is a diagram illustrating the pH range of cellulase 212.

3. Optimum pH and Stable pH range: As is shown in FIG. 1, the optimum pH is approximately 6.0, and the enzyme is characterized in that it exhibits an activity of at least 50% of the maximum activity at pH range from 4.5 to 8.5. Further, as shown in FIG. 2, the enzyme is hardly deactivated at a pH of 5.0 to 10.0 even if it is allowed to stand still at 40°C. for 30 minutes. The buffer solution used for the measurement of the optimum pH is McIlvaine buffer solution at a pH ranging from 3 to 7 or Atokins-Pantin buffer solution at a pH ranging from 7.5 to 9.0, and the buffer solution used for measurement of the stable pH range is Britton-Robinson buffer solution.

4. Measurement of Activity: An aqueous suspension containing 1.5% of Avicel (chromatography grade) or cellulose swollen with phosphoric acid is used as a substrate, and 2 ml of phosphate buffer solution (pH = 6.0) is added to 1 ml of the substrate. The mixture is pre-heated at 37°C. for 5 minutes and 1 ml of the enzyme solution is added thereto. Then the mixture is well blended and reacted for 1 hour. After the reaction, 1 ml of 1N sulfuric acid is added to the reaction mixture to stop the reaction completely, and the reaction mixture is filtered through Toyo Filter Paper No. 131 (having a diameter of 7 cm). (A mixture formed by adding 1N sulfuric acid prior to addition of the enzyme solution is used as control.) Then, 1 ml of 5% phenol is added to 1 ml of the filtrate, and 5 ml of concentrated sulfuric acid is directly poured into the mixture. The resulting mixture is agitated, cooled in water for about 10 minutes and subjected to colorimetric determination under the light of a wavelength of 485 m$\mu$. When a saccharide corresponding to 1$\mu$g of glucose is released in 1 ml of the filtrate under the above conditions, the enzyme is defined to have one unit of the activity.

Figure 3:
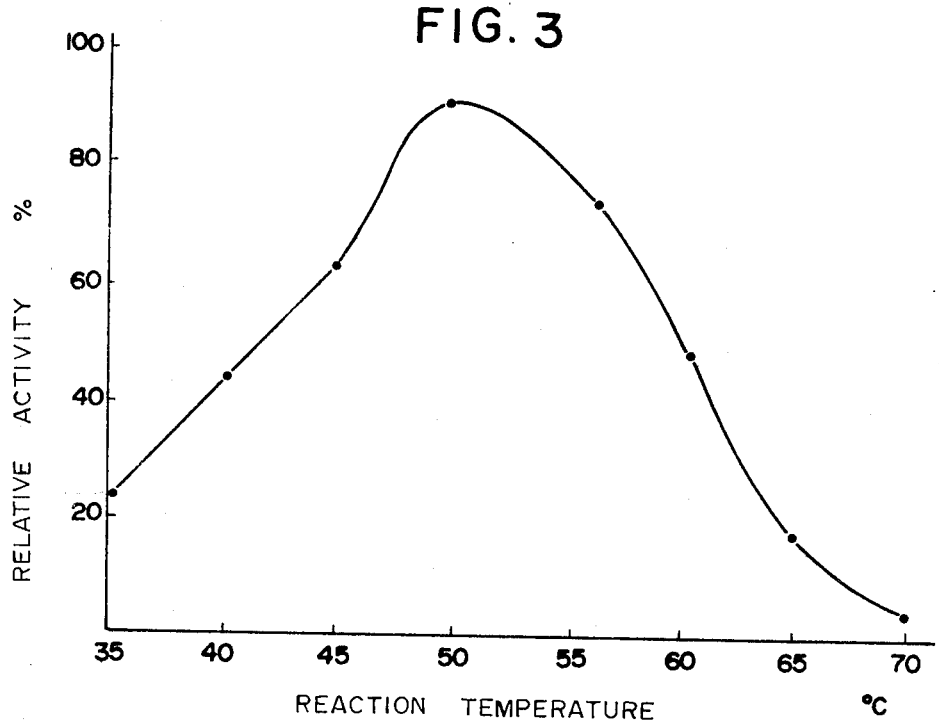
FIG. 3 is an optimum temperature curve of cellulase 212.

5. Range of Optimum Temperature: As shown in FIG. 3, the enzyme exhibits a high activity at temperatures ranging from 45° to 55°C.

Figure 4:
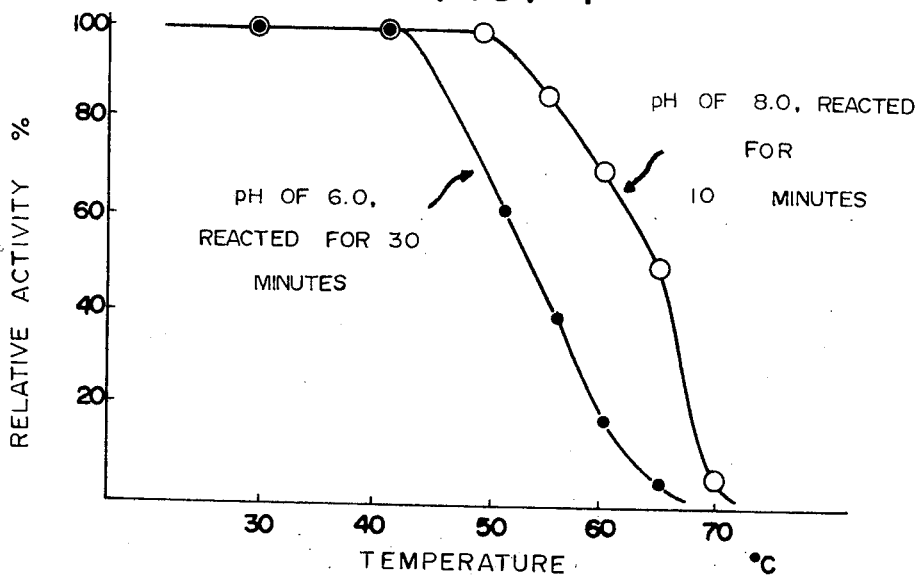
FIG. 4 is a curve showing the thermal stability of cellulase 212.

6. Deactivation by Temperature, pH and Other Conditions: As shown in FIG. 4, the enzyme has a residual activity of 60% at a pH of 6.0 even when it is treated at 50°C. for 30 minutes, and even when the enzyme is heated at 60°C. for 10 minutes at a pH of 8.0, it still retains an activity of 70%.

7. Inhibition, Activation and Stabilization: Although the activity is slightly inhibited by $Hg^{++}$, it is hardly inhibited by other metal ions. Further, no inhibition is brought about by ordinary enzyme inhibitors.

8. Purification: Crude enzyme powder containing cellulase 212 is dissolved in purified water having a volume 10 times as large as that of the powder, and the solution is adsorbed on DEAE-Spehadex A-50 buffered in advance with 0.05 M tris-hydrochloric acid buffer solution (having a pH of 8.8). The adsorbed enzyme is eluted with 0.1 M sodium chloride solution and an active fraction of cellulase 212 is collected. The collected fraction is passed through a column packed with Sephadex G-100 buffered in advance with 0.05 M tris-hydrochloric acid buffer solution of a pH of 7.0 (containing 0.1 M sodium chloride). This gel filtration procedure is repeated twice to obtain a standard sample of cellulose 212 exhibiting a single band corresponding to protein activity.

9. Molecular Weight: The enzyme has a molecular weight of about 51,000 as determined according to the gel filtration method.

10. Crystal Structure: Since the enzyme is not recovered in the crystal form, the proteinaceous singleness is determined by acrylamide disc electrophoresis. It can be confirmed that the enzyme is proteinaceously single under measurement conditions of 300 V, 5 mA, pH of 8.9 and 180 minutes.

11. Isoelectric Point: The enzyme has an isoelectric point at a pH of 4.30 to 4.40.

After due consideration of the foregoing properties in the light of the fact that none of known cellulases act on Avicel or the like at a pH of about 8.0 and the enzyme has a high stability at a pH of about 8.0, it was confirmed that the enzyme is novel, and it was named cellulase 212.

Hemicellulase 333 has the following properties.

1. Activity: The enzyme acts on hemicelluloses such as corn exoderm and spike, soybean sheath and epithelium, rice plant straw, wheat and the like, birch and elm. The enzyme decomposes and solubilizes these hemicelluloses.

2. Substrate Specificity: The enzyme acts well on hemicelluloses such as corn exoderm and spike, soybean sheath and epithelium, rice plant straw, wheat and the like, birch and elm. The enzyme acts on arabinoxylan prepared from such hemicellulose to produce xylose, xylo-oligosaccharide and a small amount of arabinose.

Figure 5:
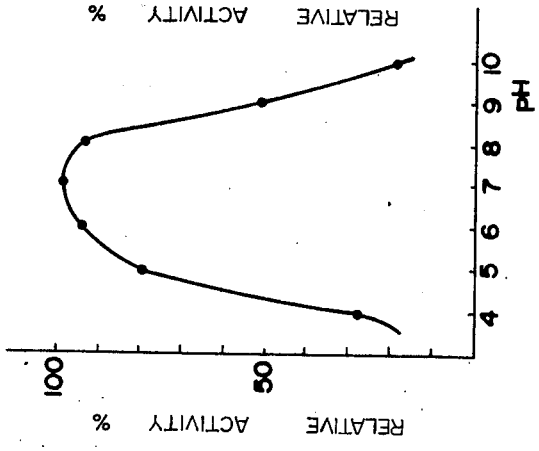
FIG. 5 is an optimum pH curve of hemicellulase 333 for decomposition of xylan.

3. Optimum pH and Stable pH Range: As is shown in FIG. 5, the optimum pH is approximately 7.0, and the enzyme is characterized in that at a pH ranging from 4.5 to 9.0 the enzyme exhibits an activity of at least 60% of the maximum activity. For this measurement the enzyme is treated at 40°C. for 30 minutes.

Figure 6:
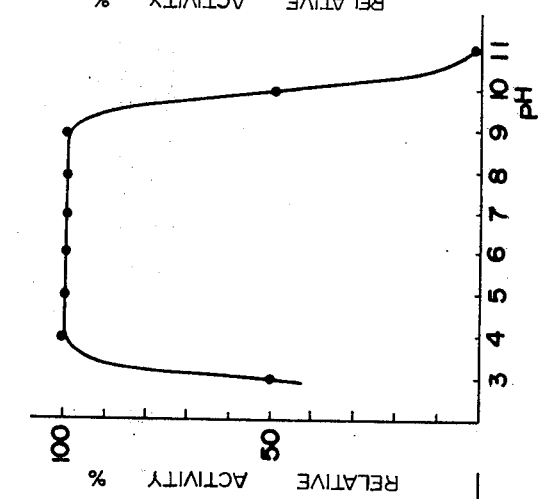
FIG. 6 is a diagram illustrating the stable pH range of hemicellulase 333.

Further, as is shown in FIG. 6, the enzyme is hardly deactivated at a pH of 4.0 to 9.0 even when it is allowed to stand still at 50°C. for 10 minutes.

The buffer solutions used for the measurement are McIlvaine buffer solution at a pH of 3 to 6, tris-hydrochloric acid buffer solution at a pH of 7 to 9 and Atkins-Pantin buffer solution at a pH of 9 to 11.

4. Measurement of Activity: 0.125 ml of tris-hydrochloric acid buffer solution having a pH of 7.0 is added to 0.125 ml of 1% hemicellulose (xylan) solution obtained by alkali extraction of rice plant straw. The mixture is preheated at 40°C. for 5 minutes, and 0.05 ml of the enzyme solution is added thereto and the reaction is conducted for 30 minutes.

The quantity of the resulting reducing sugar is determined at a wavelength of 660 m$\mu$ by the colorimetric analysis according to Somogyi-Nelson method. When the reducing power corresponding to that of 1 $\mu$g of xylose is generated for 30 minutes under the above conditions, the enzyme is defined to have one unit of the activity.

5. Range of Optimum Temperature: The enzyme has optimum activity at about 60°C.

Figure 7:
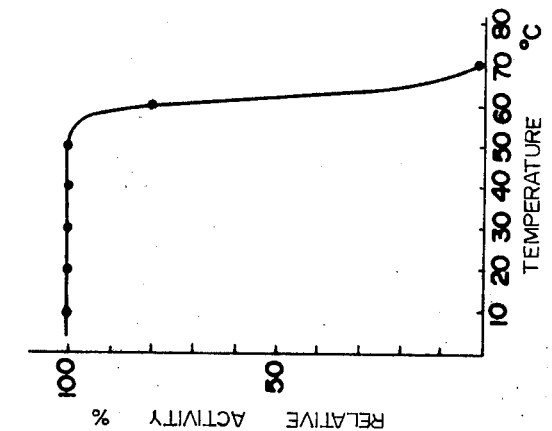
FIG. 7 is a curve showing the thermal stability of hemicellulase 333.

6. Deactivation by Temperature, pH and other Conditions: As is shown in FIG. 7, when the enzyme is treated at a pH of 6.0 for 10 minutes, the activity is reduced to 80% at 60°C. and the enzyme is completely deactivated at 70°C.

7. Activation: Influences of salts on the activity of the enzyme are as shown in the following Table II, from which it is seen that the enzyme is not activated by $Ca^{++}$ or $Cl^-$.

TABLE II

| Salt | Concentration (M) | Relative Activity |
|---|---|---|
| none (control) | — | 100 |
| NaCl | 1/30 | 78 |
| KCl | 1/30 | 80 |
| $MgSO_4$ | 1/30 | 113 |
| $CaCl_2$ | 1/30 | 91 |
| Ca-Acetate | 1/30 | 72 |

The following data were obtained by allowing a solution mixture (pH = 6.0) comprising 2 ml of 2% xylan, 2 ml of 1/10 M acetate buffer solution, 1 ml of the enzyme solution and 1 ml of the salt to stand still at 40°C. for 30 minutes and determining the amount of the reducing sugar.

8. Inhibition: The activity of the enzyme is slightly reduced by $Hg^{++}$ and $Fe^{++}$, and inhibition is caused by such metal ions.

9. Simplicity of Enzyme: The product purified by gel filtration has a single peak. A single band is obtained at the disc electrophoresis under conditions of 300 V, 5 mA, pH of 4.0 and 180 minutes. Further, the enzyme exhibits a single peak at the electrofocusing using an ampholite.

10. Molecular Weight: The enzyme has a molecular weight of about 11,000 as measured according to the gel filtration method.

11. Purification: The crude enzyme solution is subjected at a pH of 8.8 to adsorption treatment with DEAE-Sephadex A-50 to make cellulase 212 adsorbed thereon and remove it, and the non-adsorbed fraction is subjected at a pH of 8.5 to adsorption treatment with CM-Sephadex C-50, and the active fraction is eluted with 0.1 M aqueous solution of sodium chloride and adsorbed on a hydroxylapatite column treated with 0.01 M phosphate buffer solution of a pH of 6.8. Then, the active fraction is eluted with 0.05 M phosphate buffer solution of a pH of 6.8 and is thus collected. The collected active fraction is subjected to gel filtration using Biogel P-60 to obtain a purified product of hemicellulase 333.

After due consideration of the foregoing properties in light of the fact that the enzyme has a high stability at a pH of about 8.0 and none of the known hemicellulases have an activity of 50 to 70% of the maximum activity at a pH of both 4.5 and 9.0, it was confirmed that the enzyme is a novel hemicellulase and it was named hemicellulase 333.

Since the so obtained cellulase 212 and hemicellulase 333 exhibit an activity within a broad pH range of from 4.5 to 9.0, especially in an alkaline region of a pH of about 8.0, they are very effective for treatment of foodstuffs and feedstuffs or for sewage disposal.

The cellulosic material-decomposing agent of this invention comprises as an active ingredient the so prepared crude enzyme of cellulase 212 and/or hemicellulase 333 or a purified product thereof. In the case of the crude enzyme or a product purified to some extent, it is used in either the liquid or powdery form. In addition to the crude or purified enzyme of cellulase 212 and/or hemicellulase 333, the cellulosic material-decomposing agent of this invention may further comprise suitable amounts of customarily used cleaning agents such as enzymes, e.g., amylase, protease and lipase, anaerobic bacteria and aerobic bacteria, nutrients such as glucose, surface active agents, chelating agents, buffering agents, extenders and other additives.

The invention will now be described by reference to experiments in which the cellulosic material-decomposing agent of this invention was employed as a cleaning agent.

EXPERIMENT 1

Crude cellulase 212 powder obtained by purifying by the solvent precipitation method a crude enzyme solution prepared according to the method described in Example 1 given hereinbelow was added in an amount of 0.1% to a liquid (pH = 8.0) formed by digesting excrement. The mixture was treated at a temperature shown in the following Table III for a prescribed period, and the residual activity was evaluated based on the relative value to obtain results shown in the following Table III. It can be seen from Table III that cellulase 212 is hardly deactivated in the liquid and the residual activity is as high as 90% of the original activity. Accordingly, it will readily be understood that cellulase 212 is very stable in an actual sewage-treated liquid.

TABLE III

Stability of Cellulase 212 in Liquid Formed by Digesting Excrement

| Temperature (°C.) | Residual Activity (%) in Digested Liquid | | |
|---|---|---|---|
| | 0 Hour | 20 Hours | 40 Hours |
| 5 | 100 | 90.0 | 95.2 |
| room temperature | 100 | 98.1 | 102.0 |
| 37 | 100 | 91.5 | 101.0 |

EXPERIMENT 2

15 g of toilet paper (product of Nisshinbo), Avicel (product of Ashai Kasei), cellulose powder (product of Toyo Filter) or raw sewage cellulose (cellulosic material formed by subjecting raw sewage to centrifugal separation and compression dehydration and having a water content of 65%) was added as a substrate to 1 liter of a liquid (pH = 8.0) formed by digesting excrement, and the mixture was shaken for about 1 minute to make it homogeneous. Then, 5 g of the same crude cellulase 212 powder as used in Experiment 1 was added to the mixture and reaction was conducted at 37°C for 20 hours. The weight loss of the substrate solid was determined to obtain results shown in the following Table IV.

TABLE IV

Substrate-Decomposing Activity of Cellulase 212 in Excrement-Digested Liquid

| Substrate | Weight Loss (%) | |
|---|---|---|
| | 0 Hour | 20 Hours |
| toilet paper | 0 | 15.0 |
| Avicel | 0 | 7.5 |
| cellulose powder | 0 | 5.0 |
| excrement cellulose | 0 | 15.0 |

From the results shown in Table IV, it is seen that the crude cellulase 212 powder decomposes various substrates quite well even in the excrement-digested liquid.

EXPERIMENT 3

9.5 l of excrement-digested sludge was poured into each of 4 brown glass excrement digestion tanks, each having a diameter of 20 cm, a height of 32 cm and an effective volume of 10 l, and while the temperature was being maintained at 37°C., in order to form forcibly scums in each tank, 400 ml of excrement and 100 g of the same excrement cellulose as used in Experiment 2 were added to each tank once a day, and in order to keep the contents of the tank constant, 500 ml of the excrement-digested liquid was discharged from each tank once a day. 5 g of the same crude cellulase powder as used in Experiment 1 was added once a day to each of the two tanks of the above four tanks, while no enzyme was added to the remaining two tanks. The change of accumulated amounts of scum was observed with the naked eye from the outside of each tank to obtain results shown in the following Table V, from which it is seen that the thickness of scum in the crude cellulase 212-added tank is about one-third of the scum thickness in the no-cellulase-added tanks and prominent effects can be obtained by addition of cellulase 212.

TABLE V

| Enzyme | Thickness (mm) of Scum | | | | |
|---|---|---|---|---|---|
| | 1 day | 5 days | 9 days | 13 days | 17 days |
| Not added | 9 | 18 | 31 | 40 | 45 |
| | 9 | 18 | 29 | 37 | 40 |
| Added | 10 | 13 | 14 | 15 | 15 |
| | 7 | 9 | 14 | 12 | 14 |

Attainment of the effects shown in these Experiments is not at all expected by known cellulases.

The cellulosic material-decomposing agent of this invention comprising a crude enzyme powder of cellulase 212 may be added to an excrement digestion tank by various methods. For instance, it can be poured from an excrement feed inlet together with raw sewage or it can be added from a manhole in the powdery state or in the form dissolved in water.

The amount added of cellulase 212 varies depending on the purpose, namely for reducing already accumulated scums or for preventing accumulation of scums, but it is generally preferred that it be added in an amount of about 0.01 to about 1.0% based on charged excrement. Further, the cellulosic material-decomposing agent of this invention can be used effectively for treatment of materials having properties similar to those of scums of an excrement digesting tank, for example, scums formed in a digestion tank for sludges formed in a primary sedimentation tank in a water service plant or cellulosic materials causing clogging of drain pipes.

This invention will now be illustrated in more detail by reference to the following Examples.

EXAMPLE 1

90 ml of a culture medium containing 0.5% of ammonium sulfate, 1.5% of pulp flock (manufactured by Sanyo Kokusaku Pulp), 0.02% of glucose, 0.1% of yeast extract, 0.02% of $MgSO_4 \cdot 7H_2O$ and 0.2% of $K_2HPO_4$ was charged in a Sakaguchi flask, and was sterilized at 120°C. for 20 minutes and cooled. Then, 10 ml of a separately sterilized aqueous solution containing 7.0% of $NaHCO_3$ was added to the sterilized medium. Then, Aeromonas sp. No. 212 (FERM-P No. 2306; ATCC No. 31085) was inoculated on the culture medium and culturing was conducted under shaking at 37°C. After 72 hours had passed from the start of culturing, the culture medium was subjected to centrifugal separation to remove cells therefrom and obtain a crude enzyme solution of cellulase 212. The enzyme was found to have an activity of 327 $\mu$/ml.

EXPERIMENT 2

400 ml of a culture medium containing 1% of cellulose powder (manufactured by Toyo Roshi), 0.5% of polypeptone, 0.5% of yeast extract, 0.05% of glucose and 0.7% of $NaHCO_3$ was charged into a 2 l-capacity flask, and was sterilized at 120°C for 20 minutes. Aeromonas sp. No. 212 (FERM-P No. 2306; ATCC No. 31085) was precultured at 35°C for 6 hours in a culture medium containing 0.5% of glucose, 0.5% of polypeptone, 0.5% of yeast extract and 0.5% of $NaHCO_3$ and 5 ml of the culture medium was added to the above sterilized medium and culturing was conducted under shaking at 36°C for 48 hours.

After temination of culturing, the culture medium was subjected to centrifugal separation to remove cells and obtain a crude enzyme solution of cellulase 212 which was found to have an activity of 462 $\mu$/ml. (All the $NaHCO_3$ was sterilized separately and added after cooling.)

EXAMPLE 3

90 ml of a culture medium containing 0.5% of ammonium sulfate, 1% of wheat bran, 0.2% of yeast extract, 0.02% of $MgSO_4 7H_2O$ and 0.1% of $K_2HPO_4$ was charged in a Sakaguchi flask, and was sterilized at 120°C. for 20 minutes and cooled. Then, 10 ml of a separately sterilized aqueous solution of $NaHCO_3$ prepared so that the final concentration of $NaHCO_3$ was 0.7% was added to the culture medium. Aeromonas sp. No. 212 (FERM-P No. 2306; ATCC No. 31085) was inoculated on the culture medium and culturing was conducted under shaking at 37°C. After 72 hours had passed from the start of culturing, the culture medium was subjected to centrifugal separation to remove cells and obtain a crude enzyme solution of hemicellulase 333, which was found to have an activity of 1,318 $\mu$/ml.

EXAMPLE 4

400 ml of a culture medium containing 1% of rice plant straw powder, 0.5% of polypeptone, 0.5% of yeast extract and 0.7% of $NaHCO_3$ was charged into a 2 l-capacity flask, and was sterilized at 120°C. for 20 minutes and cooled. Aeromonas sp. No. 212 (FERM-P No. 2306; ATCC No. 31085) was pre-cultured at 37°C. for 8 hours, and 5 ml of the culture medium was added to the above sterilized medium. Culturing was conducted under shaking at 36°C. for 48 hours. After culturing, the culture medium was subjected to centrifugal separation to remove the cells therefrom and obtain a crude enzyme solution of hemicellulase 333, which was found to have an activity of 1506 $\mu$/ml. ($NaHCO_3$ was separately sterilized and added after cooling.)

EXAMPLE 5

90 ml. of a culture medium containing 0.5% of ammonium sulfate, 1.5% of pulp flock (manufactured by Sanyo Kokusaku Pulp), 1% of rice plant straw powder, 0.02% of glucose, 0.1% of yeast extract, 0.02% of $MgSO_4 \cdot 7H_2O$ and 0.2% of $K_2HPO_4$ was charged into a Sakaguchi flask, and was sterilized at 120°C for 20 minutes and cooled. Then, 10 ml of a separately sterilized aqueous solution containing 7.0% of $NaHCO_3$ was added to the culture medium, and Aeromonas sp. No. 212 (FERM-P No. 2306 ATTC No. 31085) was inoculated on the culture medium. Culturing was conducted under shaking at 37°C. and after 72 hours had passed from the start of culturing, the culture medium was subjected to centrifugal separation to remove cells therefrom and obtain a crude enzyme mixture solution of cellulase 212 and hemicellulase 333, which was found to have an activity of 295 $\mu$/ml as cellulase 212 and an activity of 1,200 $\mu$/ml as hemicellulase 333.

EXAMPLE 6

The pH of the crude enzyme solution obtained in Example 5 was adjusted to 8.8, and 2,000 ml of the enzyme solution was treated with DEAE-Sephadex A-50 to make cellulase 212 adsorb thereon. The pH of the effluent was adjusted to 8.5 and adsorbed on CM-Sephadex C-50. After washing, elution was effected with 0.1 M aqueous solution of sodium chloride, and the eluted active fraction was adsorbed on a hydroxylapatite pH of 6.8. The active fraction was eluted with 0.05 M phosphate buffer solution having a pH of 6.8 and was thus collected. Then, the eluted solution was subjected to gel filtration using Biogel P-60 to obtain a solution of purified hemicellulase 333. The amount of the so obtained aqueous solution was 34 ml and its activity was found to be 15,421 $\mu$/ml.

The cellulase 212 adsorbed on DEAE-Sephadex A-50 was eluted with 0.5 M aqueous solution of sodium chloride and was further adsorbed at a pH of 7.5 on DEAE-Sephadex A-50. The active fraction of cellulase 212 was collected by elution with 0.1 M aqueous solution of sodium chloride, and it was passed through a column packed with Sephadex G-100 buffered with 0.05 M tris-hydrochloric acid buffer solution of a pH of 7.0 (containing 0.1 M of sodium chloride). This gel filtration procedure was repeated twice to obtain 204 ml of a solution of purified cellulase 212, which was found to have an activity of 1,151 $\mu$/ml.

EXAMPLE 7

Crude cellulase 212 powder obtained by solvent precipitation of the crude enzyme solution obtained in Example 1 was used as the cellulosic material-decomposing agent of this invention as it was.

50 Kg (0.1% based on excrement fed) of this decomposing agent was fed together with excrement into an excrement opening of an excrement digestion tank of a capacity of 800 m³ in which scums were formed in a thickness of 150 cm and the amount generated of gases was reduced to one-third of the ordinary amount gererated of gases. In addition, 10 Kg of the decomposing agent was fed into a manhole of said tank. Then, 10 Kg of the decomposing agent was added from the excrement opening once a day.

After passage of 10 days from the start of addition of the cellulosic material-decomposing agent of this invention, the scums substantially collapsed, and the amount generated of gases was restored to the ordinary level on the 23rd day from the start of addition of the decomposing agent of this invention.

EXAMPLE 8

50 parts by weight of crude cellulase 212 powder obtained in Example 6, 10 parts by weight of primary sodium phosphate, 35 parts by weight of secondary sodium phosphate and 5 parts by weight of polyoxyethylene glycol wwre sufficiently blended to obtain a cleaning agent of this invention.

When about 10 g of the so obtained cleaning agent was poured together with a small amount of water into a household drain pipe in which drain did not flow well because it was clogged with cellulosic materials and the addition was repeated several times per day, the clogging cellulosic materials could be removed effectively.

EXAMPLE 9

9.6 l of seed sludge for anaerobic digestion was charged into each of 3 brown glass digestion tanks having a diameter of 20 cm, a height of 32 cm and an effective volume of 10 l, and while the temperature was being maintained at 37°C. (water content of 94%; organic material content of 3.8%) 400 ml of sludge, formed in a primary sedimentation tank in a service water plant, was added to each digestion tank once a day, and 400 ml of the digested liquid was discharged from the tank so as to keep the content of the tank constant. When 20 days had passed from the start of operation of the digestion tanks, and enzyme mixture powder obtained by solvent precipitation of the crude enzyme mixture solution of cellulase 212 and hemicellulase 333 obtained in Example 5 was added in amounts of 3 g and 1 g to digestion tanks No. 1 and No. 2, respectively while no enzyme powder was added to digestion tank No. 3.

When 50 days had passed from the start of operation of the digestion tanks, the thickness of scums was 35 mm in tank No. 3 (control), whereas the scum thickness was 8 mm in tank No. 2 and no scum was substantially formed in tank No. 1. From the so obtained results, it was confirmed that the cellulosic material-decomposing agent of this invention has a very high effect.

It will be obvious to those skilled in the art that various changes may be made without departing from the scope of the invention and the invention is not to be considered limited to what is described in the specification or shown in the drawing.

What is claimed:

1. A process for preparing cellulase 212 comprising:
   aerobically culturing Aeromonas sp. No. 212, FERM-P No. 2306, ATCC No. 31085, in a culture medium containing a nitrogen source, a carbon source and a nutrient while maintaining the pH of the culture medium at 6–10 until cellulase is produced and accumulated therein; and
   separating and recovering the cellulase produced and accumulated in the culture medium during the culturing step.

2. A process in accordance with claim 1, wherein the pH is adjusted to 7–9 at the initial stage of the culturing.

3. A process in accordance with claim 1 wherein, said culturing step is conducted at 30°–45°C. for 2–5 days.

4. A process for preparing hemicellulase 333 comprising:
   aerobically culturing Aeromonas sp. No. 212, FERM-P No. 2306, ATCC No. 31085, in culture medium containing a nitrogen source, a carbon source and a nutrient while maintaining the pH of the culture medium at 6–10 until hemicellulase is produced and accumulated therein; and separating and recovering the hemicellulase produced and accumulated in the culture medium during the culturing step.

5. A process in accordance with claim 4, wherein said culturing step is conducted at 30°–45°C. for 2–5 days.

6. A process for preparing both cellulase 212 and hemicellulase 333, comprising:

aerobically culturing Aeromonas sp. No. 212, FERM-P No. 2306, ATCC No. 31085, in a culture medium containing a nitrogen source, a carbon source and a nutrient while maintaining the pH of the culture medium at 6–10 until both cellulase and hemicellulase are produced and accumulated therein; and recovering the cellulase and hemicellulase produced and accumulated in the culture medium during the culturing step.

* * * * *